United States Patent [19]

Campbell et al.

[11] Patent Number: 4,656,174

[45] Date of Patent: Apr. 7, 1987

[54] QUINOLINE THERAPEUTIC AGENTS

[75] Inventors: Simon F. Campbell; John D. Hardstone, both of Deal, England

[73] Assignee: Pfizer Inc., New York, N.Y.

[21] Appl. No.: 515,095

[22] Filed: Jul. 19, 1983

[30] Foreign Application Priority Data

Jul. 24, 1982 [GB] United Kingdom ............... 8221457

[51] Int. Cl.$^4$ .................. A61K 31/495; C07D 401/04
[52] U.S. Cl. .................................... 514/254; 544/209;
544/238; 544/295; 544/363; 546/144; 546/159
[58] Field of Search ............... 544/363; 424/250;
514/254

[56] References Cited

U.S. PATENT DOCUMENTS

| | | | |
|---|---|---|---|
| 3,511,836 | 5/1970 | Hess | 514/254 |
| 3,517,005 | 6/1970 | Cronin et al. | 514/252 |
| 3,960,861 | 6/1976 | Danilewicz et al. | 514/252 |
| 4,035,367 | 7/1977 | Simpson | 544/363 |
| 4,188,390 | 2/1980 | Campbell | 514/252 |
| 4,237,135 | 12/1980 | Uno et al. | 544/363 |

FOREIGN PATENT DOCUMENTS 56836 12/1979 Finland.

OTHER PUBLICATIONS

Thaler, "Chemical Abstracts", vol. 93, 1980, col. 93:186404h.

Primary Examiner—Glennon H. Hollrah
Assistant Examiner—James H. Turnipseed
Attorney, Agent, or Firm—Charles J. Knuth; Peter C. Richardson

[57] ABSTRACT

A series of novel 2-substituted 4-amino-6,7-dimethoxyquinoline derivatives have been prepared, including their pharmaceutically acceptable acid addition salts. These particular compounds are useful in therapy as highly potent antihypertensive agents. Preferred member compounds include 4-amino-2-[4-(2-furoyl)piperazine-1-yl]-6,7-dimethoxyquinoline, 4-amino-2-[4-(1,4-benzodioxan-2-carbonyl)piperazin-1-yl]-6,7-dimethoxyquinoline and 4-amino-6,7-dimethoxy-2-(6,7-dimethoxy-1,2,3,4-tetrahydroisoquinol-2-yl)quinoline, respectively. Methods for preparing these compounds from known starting materials are provided.

7 Claims, No Drawings

QUINOLINE THERAPEUTIC AGENTS

BACKGROUND OF THE INVENTION

This invention relates to therapeutic agents which are novel derivatives of 4-amino-6,7-dimethoxyquinoline. Such compounds are useful as regulators of the cardiovascular system and, in particular, in the treatment of hypertension.

SUMMARY OF THE INVENTION

The novel compounds according to the invention are those having the formula:

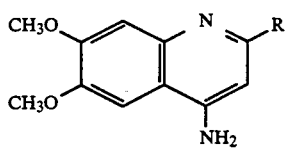

and their pharmaceutically acceptable acid addition salts, wherein R is $-N(C_1-C_4$ alkyl$)_2$, piperidino, 6,7-dimethoxy-1,2,3,4-tetrahydroisoquinol-2-yl or a group of the formula

where Y is H, $C_1-C_6$ alkyl, aryl, $C_1-C_4$ alkyl substituted by aryl, or a nitrogen-containing aromatic heterocyclic group attached to the adjacent nitrogen atom of the piperazinyl group by a carbon atom, or Y is selected from (a) $-COR^1$ where $R^1$ is $C_1-C_6$ alkyl, $C_1-C_4$ alkyl substituted by aryl, $C_3-C_6$ cycloalkyl, ($C_3-C_6$ cycloalkyl)-methyl, aryl, styryl or a heterocyclic group;

(b) $-CONHR^2$ where $R^2$ is $C_1-C_6$ alkyl, aryl, $C_1-C_4$ alkyl substituted by aryl, ($C_2-C_4$ alkenyl)methyl, $C_3-C_6$ cycloalkyl or ($C_3-C_6$ cycloalkyl)methyl; and (c) $-COOR^3$ where $R^3$ is $C_1-C_6$ alkyl, $C_1-C_4$ alkyl substituted by aryl, $C_2-C_4$ alkyl substituted other than on an α-carbon atom by hydroxy, $C_3-C_6$ cycloalkyl, ($C_3-C_6$ cycloalkyl)methyl, ($C_2-C_4$ alkenyl)methyl, or aryl.

The preferred aryl groups are phenyl and naphthyl, and said phenyl group can be substituted by, for example, 1 or 2 substituents each selected from halo, $CF_3$, $C_1-C_4$ alkyl and $C_1-C_4$ alkoxy, or by a single methylenedioxy group.

"Halo" means F, Cl, Br or I.

Alkyl, alkoxy and alkenyl groups can be straight or, when appropriate, branched chain. Preferred alkyl groups have 1 to 4 carbon atoms.

Pharmaceutically acceptable acid addition salts of the compounds of the invention are those formed from acids which form non-toxic acid addition salts containing pharmaceutically acceptable anions, such as the hydrochloride, hydrobromide, sulphate or bisulphate, phosphate or acid phosphate, acetate, maleate, fumarate, succinate, lactate, tartrate, citrate, gluconate and p-toluenesulphonate salts.

Examples of $R^1$ include

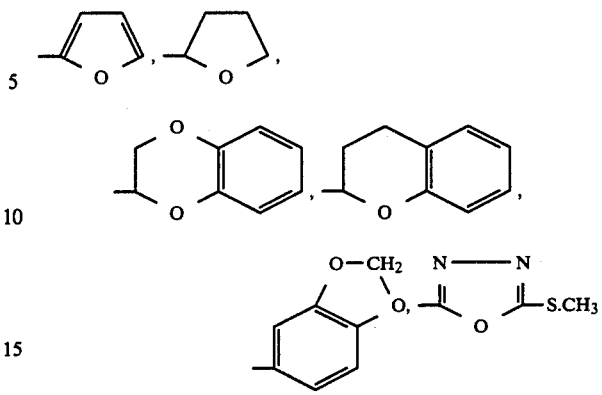

phenyl, p-fluorophenyl, methyl, cyclopropylmethyl, cyclopentyl, styryl, 2-naphthyl and 2-quinolyl.

Examples of $R^2$ include phenyl, cyclopropylmethyl, benzyl, n-propyl and allyl.

Examples of $R^3$ include ethyl, $-CH_2CH(CH_3)_2$, $-CH_2C(CH_3)_2(OH)$, cyclopropylmethyl, p-fluorophenyl, benzyl and $-CH_2.C(CH_3)=CH_2$.

When Y is said nitrogen-containing aromatic heterocyclic group, this includes, for example, the following:

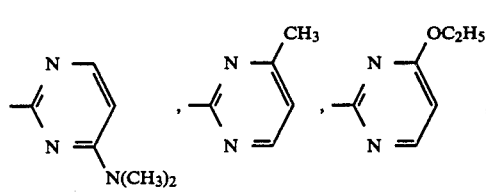

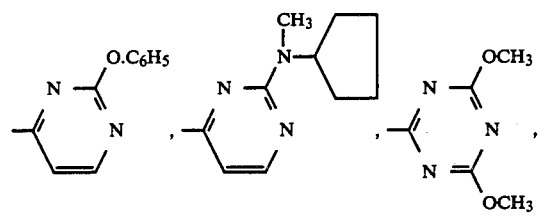

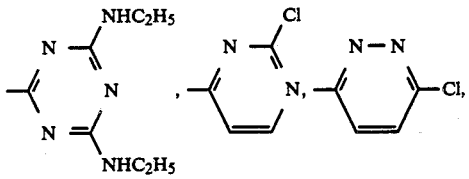

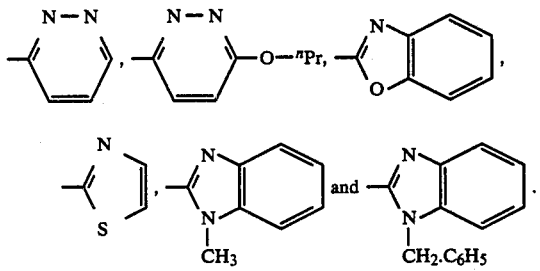

Detailed Description of the Invention

The compounds of the formula (I), can be prepared as follows:

(1) An N-(1R-substituted-ethylidene)-2-cyano-4,5-dimethoxyaniline (II) may be cyclised to form the correspondingly substituted 4-amino-6,7-dimethoxyquinoline (I):

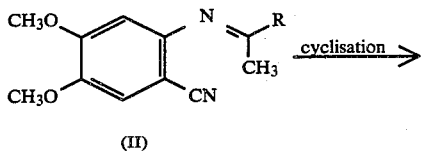

(II)

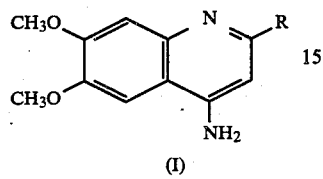

(I)

The cyclisation can be carried out using a Lewis acid, e.g. zinc chloride, or a base, e.g. lithium diisopropylamide (LDA). Zinc chloride is preferred when R is said tetrahydroisoquinolyl group or an N-aralkyl-piperazino group. The reaction with zinc chloride is typically carried out by heating the reactants, preferably at reflux, in a suitable organic solvent, e.g. dimethylacetamide, for up to about 4 hours. The reaction with LDA is typically carried out at low temperature (e.g. −70° C.) in a suitable organic solvent, e.g. tetrahydrofuran, following which the reaction mixture is allowed to warm to room temperature. In some cases using LDA, heating may be necessary to complete the reaction. The product can then be isolated and purified conventionally.

The compounds (II) are obtainable conventionally as is illustrated in the following Preparations. Typical methods are outlined as follows:

(a) For compounds where R is as defined above in this method except for unsubstituted piperazinyl (Y=H):

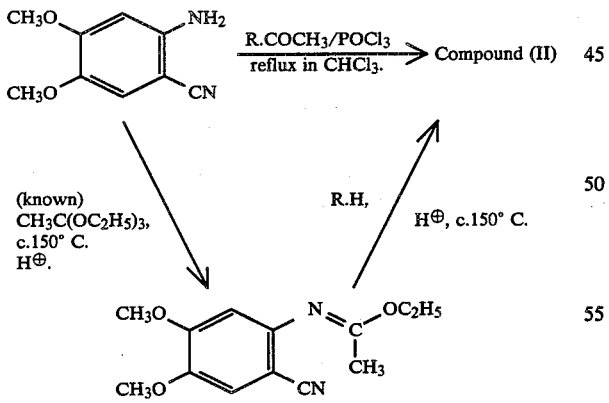

(b) For compounds in which R is unsubstituted piperazinyl:

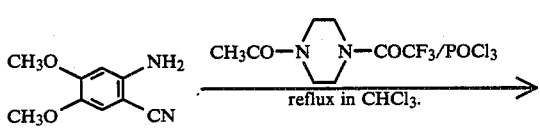

-continued

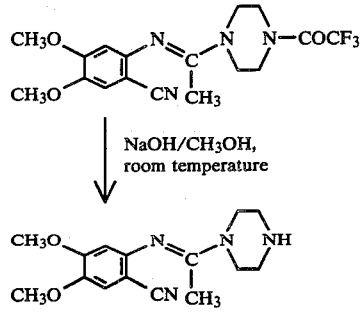

(2) The Compound in which R is

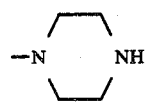

can also be prepared by debenzylation of the corresponding 4-benzylpiperazin-1-yl compound, itself preparable via route (1) above. This can be carried out conventionally using, e.g., H₂ over a Pd/C catalyst.

(3) Compounds in which Y is —COR¹ can be prepared as follows:

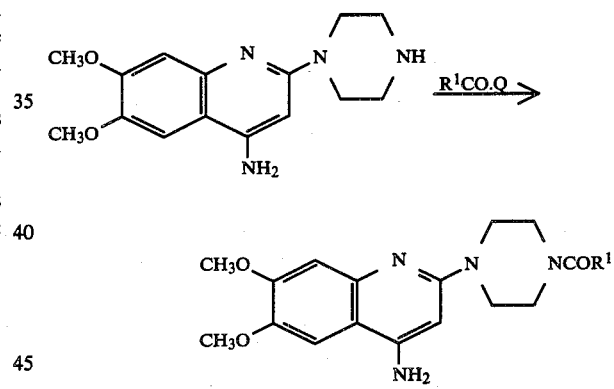

Q is a facile leaving group, preferably Cl.

The reaction can be carried out conventionally. When Q is Cl, the presence of a tertiary amine acid acceptor such as triethylamine is desirable. Generally, heating is unnecessary. Typically the reactants are stirred together in a suitable organic solvent, e.g. chloroform, at 5°–10° C. for 1–2 hours. The reaction mixture can then be allowed to attain room temperature and the product isolated conventionally.

(4) Compounds in which Y is —CONHR² can be prepared as follows:

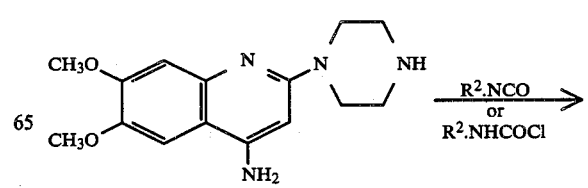

-continued

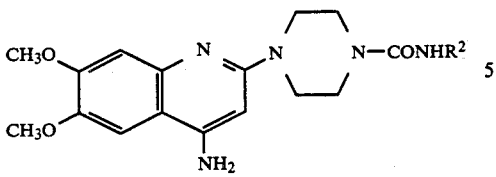

-continued

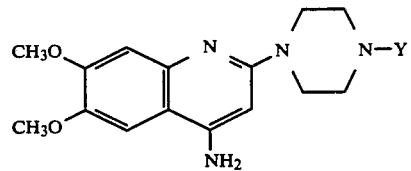

When an isocyanate R².NCO is used, the reaction can again be carried out conventionally, e.g. by stirring the reactants together for a few hours (e.g. 3–6 hours) in a suitable organic solvent, e.g. chloroform. Heating is again generally unnecessary; the product can be isolated routinely.

When a carbamoyl chloride R².NHCOCl is used, this may be generated in situ by the action of phosgene on the amine R².NH₂ as its hydrochloride salt in the presence of an acid acceptor such as triethylamine in a dry, cooled organic solvent, such as chloroform at −40°. After allowing this to warm to ambient temperature and removing excess phosgene, a solution of the piperazino-quinoline in the same solvent is added slowly with cooling, the mixture stirred until reaction is complete and the product isolated routinely.

(5) Compounds in which Y is —COOR³ can be prepared as follows:

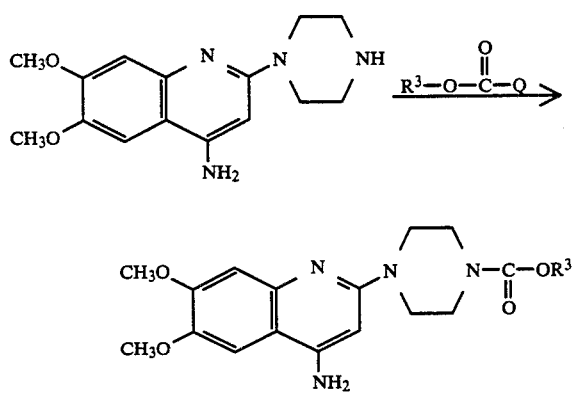

where Q is a facile leaving group, preferably Cl. Typically the reaction is carried out by stirring the reactants together for a few hours in a suitable organic solvent such as chloroform, preferably, when Q is Cl, in the presence of an acid acceptor such as triethylamine. Heating is not generally necessary, and the product can be isolated in a routine manner.

(6) Compounds in which Y is said nitrogen-containing aromatic heterocyclic group can be prepared as follows:

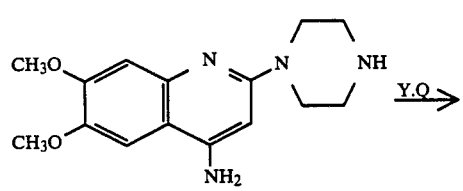

where Q is a facile leaving group, preferably Cl. The reaction is typically carried out by heating the reactants, preferably under reflux, in a suitable organic solvent, e.g. n-butanol, for up to about 24 hours, after which the product can be isolated conventionally.

Certain compounds of the invention can be converted to other compounds of the invention by conventional means, e.g. a chlorine substituent on an aromatic heterocyclic group Y can be replaced by a phenoxy group or an amino group by reaction with phenol or an amine, respectively, under conditions well known in the art, and an alkenyl-methyl group R³ can be converted to a hydroxyalkyl-methyl group by treatment with concentrated sulphuric acid, as is also well known in the art.

The pharmaceutically acceptable acid addition salts of the comounds of the formula (I) can be prepared by conventional procedurs, e.g. by reacting the free base with the appropriate acid in an inert organic solvent, and collecting the resulting precipitate of the salt by filtration or by evaporation of the reaction mixture. If necessary, the product may then be recrystallised to purify it.

When the compounds of the invention contain an asymmetric centre, the invention includes both the resolved and unresolved forms. Resolution of optically active isomers can be carried out according to conventional prior art methods.

The antihypertensive activity of the compounds of the formula (I) is shown by their ability to lower the blood pressure of conscious spontaneously hypertensive rats and conscious renally hypertensive dogs, when administered orally at doses of up to 5 mg/kg.

The compounds of the formula (I) and their salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavouring or colouring agents. They can be injected parenterally, for example, intramuscularly, intravenously or subcutaneously. For parenteral administration, they are best used in the form of a sterile aqueous solution which may contain other solutes, for example, enough salt or glucose to make the solution isotonic.

Thus the invention also provides a pharmaceutical composition comprising a compound of the formula (I) or pharmaceutically acceptable acid addition salt thereof together with a pharmaceutically acceptable diluent or carrier.

It also provides a compound of the formula (I), or a pharmaceutically acceptable acid addition salt thereof, for use in treating hypertension in a human being.

The compounds of the formula (I) and their salts can be administered to humans for the treatment of hypertension by either the oral or parenteral routes, and will be administered orally at dosage levels within the range 1 to 50 mg/day for an average adult patient (70 kg), given in a single dose or up to 3 divided doses. Intravenous dosage levels will be 1/5th to 1/10th of the daily oral dose. Thus for an average adult patient, individual oral doses in tablet or capsule form will be approximately in the range from 1 to 25 mg of the active compound. It should however be stated that variations will necessarily occur depending on the weight and condition of the subject being treated and the particular route of administration chosen as will be known to those skilled in the art.

The invention yet further provides a method of treating a human being having hypertension, which comprises administering to the human an antihypertensive amount of a compound of the formula (I) or pharmaceutically acceptable acid addition salt thereof or pharmaceutical composition as defined above.

The following Examples illustrate the invention. All temperatures are in °C.:

EXAMPLE 1

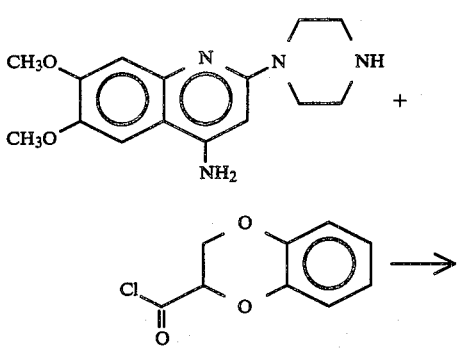

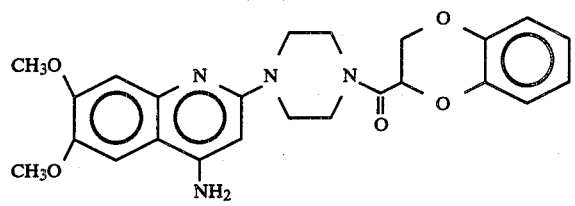

A solution of 1,4-benzodioxan-2-carbonyl chloride (0.75 g) in chloroform (10 ml) was added dropwise to a stirred solution of 4-amino-6,7-dimethoxy-2-(piperazin-1-yl)quinoline (1.0 g) in chloroform (50 ml) with triethylamine (1.06 g) at 5°–10°. The reaction was stirred at 5°–10° for one hour, then allowed to attain room temperature and stirred overnight. The mixture was then evaporated in vacuo and the residue partitioned between chloroform (50 ml) and sodium carbonate solution (10%, 50 ml). The chloroform layer was separated, the aqueous phase extracted with chloroform (2×50 ml), the extracts combined, washed with brine, dried (Na₂SO₄) and evaporated in vacuo. The residue was then taken up in chloroform and chromatographed on silica (Merck 9385, 60 g) eluting with chloroform/methanol (100:0→97:3). A solution of the purified product in chloroform was treated with ethereal hydrogen chloride, evaporated in vacuo and the residue recrystallised from isopropanol to give 4-amino-2-[4-(1,4-benzodioxan-2-carbonyl)piperazin-1-yl]-6,7-dimethoxyquinoline hydrochloride hydrate (0.28 g), m.p. 201°.

Analysis %: Found: C, 56.7; H, 5.4; N, 11.0. Calculated for $C_{24}H_{26}N_4O_5 \cdot HCl \cdot H_2O$: C, 57.1; H, 5.8; N, 11.1.

EXAMPLES 2 TO 11

The following compounds were prepared similarly to Example 1, starting from the same quinoline and the appropriate acid chloride as indicated. After chromatography, the product was crystallised from the solvent shown in each case.

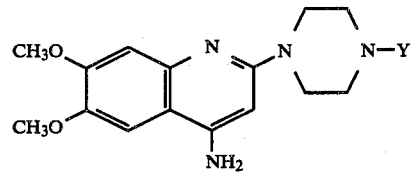

| Example No. | Y | Form Isolated and m.p. (°C.) | Prepared from, and recrystallised from | Analysis % (Theoretical in brackets) C | H | N |
|---|---|---|---|---|---|---|
| 2 | —C(=O)—(2-furyl) | Hydrochloride ¼ hydrate, 270° | 2-furoyl chloride, MeOH/Et₂O | 56.7 (56.7 | 5.5 5.6 | 13.5 13.2) |
| 3 | —C(=O)—phenyl | Hydrochloride ½ hydrate 301° | benzoyl chloride, MeOH | 60.2 (60.3 | 5.7 6.0 | 12.7 12.8) |
| 4 | —C(=O)—CH₃ | HCl.1.5H₂O, 215–220° C. | Acetyl chloride, (i) EtOH (ii) MeOH/EtOH | 52.1 (51.8 | 6.5 6.7 | 14.1 14.2) |

-continued

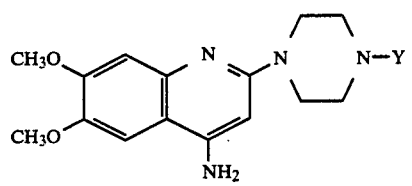

| Example No. | Y | Form Isolated and m.p. (°C.) | Prepared from, and recrystallised from | Analysis % (Theoretical in brackets) C | H | N |
|---|---|---|---|---|---|---|
| 5 | cyclopentyl-C(O)- | HCl, 292° C. | Cyclopentane carbonylchloride, IPA/MeOH 4:1 | 59.8 (59.9 | 7.0 6.9 | 13.5 13.3) |
| 6 | cinnamoyl (PhCH=CH-C(O)-) | HCl.0.5H₂O, 240–241° C. | cinnamoyl chloride, EtOH | 61.8 (62.1 | 6.0 6.1 | 12.0 12.1) |
| 7 | 2-naphthoyl | HCl.0.5H₂O, >300° C. | 2-naphthoyl chloride, MeOH/Et₂O | 64.3 (64.0 | 5.8 5.8 | 11.6 11.5) |
| 8 | quinoline-2-carbonyl | HCl.1.5H₂O, 238–239° C. | Quinoline-2-carbonyl chloride EtOH/MeOH 1:1 | 59.3 (59.2 | 5.4 5.8 | 13.9 13.8) |
| 9 | piperonoyl (1,3-benzodioxol-5-yl-C(O)-) | HCl.0.5H₂O, 300–301° C. | Piperonoyl chloride, MeOH | 57.2 (57.3 | 5.4 5.4 | 11.6 11.6) |
| 10 | p-fluorobenzoyl | HCl. 274° C. | p-Fluorobenzoyl chloride, hexane IPA | 58.5 (59.1 | 5.7 5.4 | 12.3 12.5) |
| 11 | chroman-2-carbonyl | HCl.H₂O, 251–252° C. | chroman-2-carbonylchloride, IPA | 59.6 (59.7 | 5.9 6.2 | 11.2 11.1) |

EXAMPLE 12

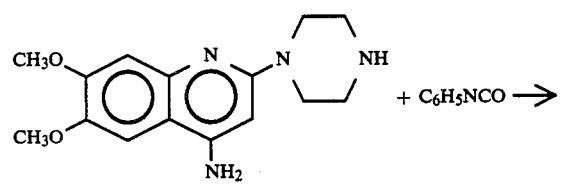 + C₆H₅NCO →

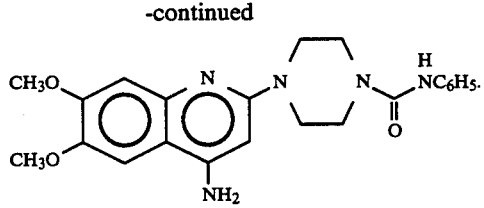

Phenylisocyanate (1.1 g) was added to a stirred suspension of 4-amino-6,7-dimethoxy-2-(piperazin-1-yl)quinoline (0.72 g) in chloroform (25 ml) at room temperature and the reaction mixture was stirred for 4 hours. The mixture was evaporated in vacuo, the residue taken up in methanol-chloroform and treated with ethereal hydrogen chloride. The crude product was purified by chromatography on silica gel eluting with methylene chloride followed by chloroform/methanol and then recrystallised from methanol/ether to give 4-amino-6,7-dimethoxy-2-[4-(N-phenylcarbamoyl)piperazin-1-yl]quinoline dihydrochloride (0.18 g), m.p. 235°.

Analysis %: Found: C, 55.1; H, 5.7; N, 14.7. Calculated for $C_{22}H_{25}N_5O_3 2HCl$: C, 55.0; H, 5.7; N, 14.6.

EXAMPLES 13 TO 15

The following compounds were prepared similarly to Example 12, using the appropriate isocyanate $R^2.NCO$ as indicated, and the product crystallised from the solvent shown in each case.

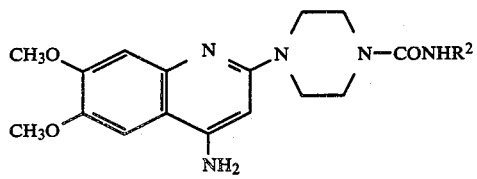

In Example 13 chromatography was not necessary, while in Examples 14 and 15 the reaction mixtures were purified as in Example 16, i.e. chromatographed as the free base and (in the case of Example 14) then converted to the hydrochloride.

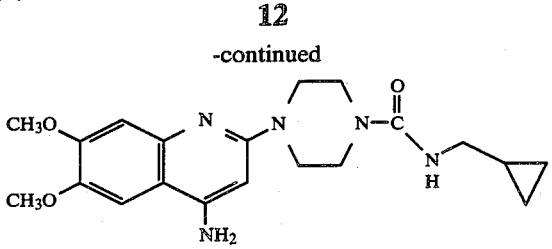

(Aminomethyl)cyclopropane hydrochloride (0.25 g) and triethylamine (0.61 g) in $P_2O_5$-dried chloroform (15 ml) was added dropwise to a stirred solution of phosgene in toluene (12.5%, 2.6 ml) at −40°. The reaction mixture was allowed to warm to room temperature and stirred for 0.5 hours. Excess phosgene was removed in a steam of nitrogen then a solution of 4-amino-6,7-dimethoxy-2-(piperazin-1-yl)quinoline (0.3 g) in $P_2O_5$-dried chloroform (30 ml) was added dropwise at 10° and the reaction mixture stirred at room temperature for 1.5 hours. Sodium carbonate solution (10%, 10 ml) was then added and the chloroform layer separated. The aqueous phase was extracted with chloroform, the organic phases combined, washed with water, dried ($MgSO_4$) and evaporated in vacuo. The residue was then taken up in methylene chloride and chromatographed on silica (Merck 9385, 85 g) eluting with methylene chloride/methanol (100:0→85:15). A solution of the purified product in methylene chloride was treated with ethereal hydrogen chloride, evaporated in vacuo and the residue recrystallised from isopropanol to give 4-amino-2-[4-(N-cyclopropylmethylcarbamoyl)piperazin-1-yl]-6,7-dimethoxyquinoline hydrochloride hemi-

| Example No. | $R^2$ | Form Isolated and m.p. (°C.) | Prepared from, and recrystallised from | Analysis % (Theoretical in brackets) | | |
|---|---|---|---|---|---|---|
| | | | | C | H | N |
| 13 | $-CH_2CH_2CH_3$ | HCl.1.5H$_2$O 200° (d) | n-propyl isocyanate, MeOH/Et$_2$O | 54.0 (54.5 | 6.8 7.0 | 16.7 16.7) |
| 14 | $-CH_2C_6H_5$ | HCl, 269-270° C. | Benzyl isocyanate, IPA | 59.8 (60.3 | 6.1 6.2 | 14.9 15.3) |
| 15 | $-CH_2CH=CH_2$ | H$_2$O, 178-181° C. (d) | Allyl isocyanate, EtOAc/CH$_2$Cl$_2$/ hexane | 58.3 (58.6 | 6.7 7.0 | 17.8 18.0) | hydrate (165 mg), m.p. 220°-223° (d).

Analysis %: Found: C, 55.6; H, 6.5; N, 16.4. Calculated for $C_{20}H_{27}N_5O_3.HCl,0.5H_2O$: C, 55.7; H, 6.8; N, 16.3.

EXAMPLE 16

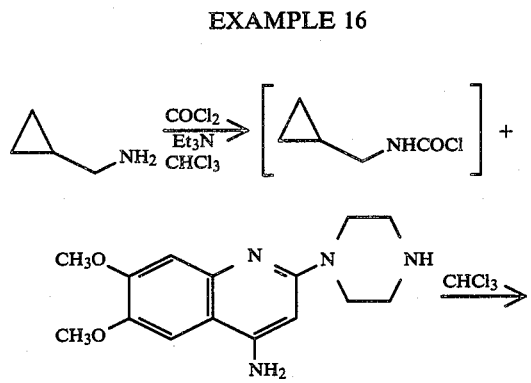

EXAMPLE 17

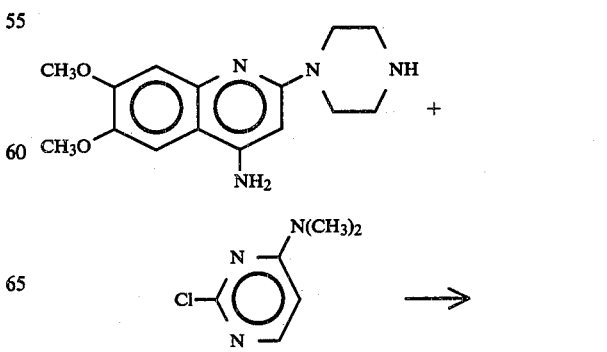

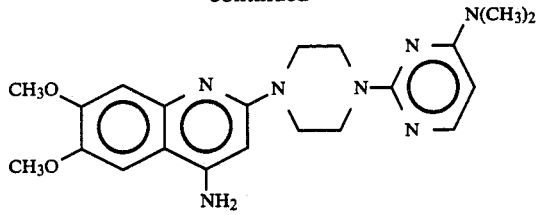

4-Amino-6,7-dimethoxy-2-(piperazin-1-yl)quinoline (1.26 g) and 2-chloro-4-dimethylaminopyrimidine (0.76 g) in n-butanol (60 ml) were heated under reflux for 16 hours. The mixture was then evaporated in vacuo, the residue partitioned between chloroform and sodium carbonate solution (10%) and the aqueous phase extracted with chloroform. The combined extracts were washed with water, dried ($Na_2SO_4$), evaporated in vacuo and the residue chromatographed on silica gel (Merck 9385). Elution with chloroform-methanol (100:0→95.5) followed by treatment of the product with ethereal hydrogen chloride and recrystallisation from methanol gave 4-amino-6,7-dimethoxy-2-[4-(4-dimethylaminopyrimidin-2-yl)piperazin-1-yl]quinoline dihydrochloride dihydrate (0.19 g), m.p. 260°–263°.

Analysis %: Found: C, 48.4; H, 5.8; N, 18.9. Calculated for $C_{21}H_{27}N_7O_2.2HCl.2H_2O$: C, 48.7; H, 6.4; N, 18.9.

EXAMPLES 18 TO 26

The following compounds were prepared similarly to Example 18, using the appropriate halogenated heterocyclic compound YQ as indicated, and the product crystallised from the solvent shown in each case. In Example 20 chromatography was not necessary.

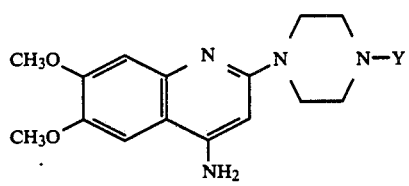

| Example No. | Y | Form Isolated and m.p. (°C.) | Prepared from, and recrystallised from | Analysis % (Theoretical in brackets) | | |
|---|---|---|---|---|---|---|
| | | | | C | H | N |
| 18 | benzoxazol-2-yl | HCl.2H₂O 271° | 2-chlorobenzoxazole, MeOH | 55.6 (55.3 | 5.5 5.9 | 14.2 14.7) |
| 19 | 4-methylpyrimidin-2-yl | 2HCl.CH₃OH, 282–283° C. | 2-chloro-4-methylpyrimidine, MeOH | 51.7 (52.0 | 6.1 6.2 | 17.8 17.3) |
| 20 | 4-ethoxypyrimidin-2-yl | HCl.2H₂O 267–269° C. | 2-chloro-4-ethoxypyrimidine EtOH | 51.7 (52.2 | 5.8 6.5 | 17.2 17.4) |
| 21 | 4,6-dimethoxy-1,3,5-triazin-2-yl | 2HCl.1.5H₂O 266–268° C. dec. | 6-chloro-2,4-dimethoxy-triazine, MeOH | 45.2 (45.5 | 5.1 5.7 | 18.5 18.6) |
| 22 | 4,6-bis(ethylamino)-1,3,5-triazin-2-yl | 2HCl 1.5H₂O, 247–248° C. | 6-chloro-2,4-bis(ethylamino) triazine, MeOH | 47.8 (47.7 | 6.2 6.6 | 22.5 22.8) |
| 23 | 6-chloropyridazin-3-yl | H₂O 262–266° C. dec. | 3,6-dichloropyridazine, not recryst. | 54.3 (54.5 | 5.2 5.5 | 19.9 20.1) |

-continued

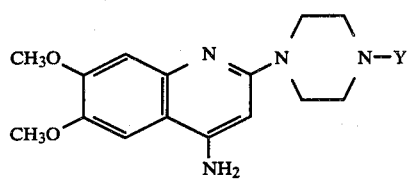

| Example No. | Y | Form Isolated and m.p. (°C.) | Prepared from, and recrystallised from | Analysis % (Theoretical in brackets) | | |
|---|---|---|---|---|---|---|
| | | | | C | H | N |
| 24 | (2-thiazolyl) | 2HCl, 244–247° C. dec. | 2-Bromothiazole, MeOH | 49.2 (48.7 | 5.2 5.2 | 15.8 15.8) |
| 25 | (1-methylbenzimidazol-2-yl) | 2HCl 3H$_2$O, 245–252° C. dec. | 2-chloro-1-methylbenz-imidazole, MeOH | 50.3 (50.6 | 5.5 6.3 | 14.8 15.4) |
| 26 | (2-chloropyrimidin-4-yl) | 0.5H$_2$O, 245–247° C. | 2,4-dichloro-pyrimidine, (1) not recryst. | 55.2 (55.7 | 5.5 5.4 | 20.2 20.5) |

(1) carried out in ethanol at room temperature in the presence of triethylamine.

EXAMPLE 27

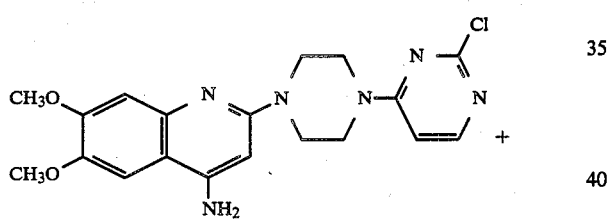

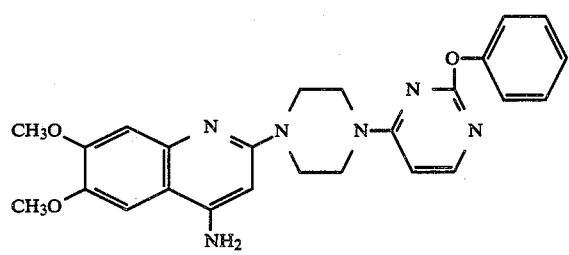

4-Amino-2-[4-(2-chloropyrimidin-4-yl)piperazin-1-yl]-6,7-dimethoxyquinoline hemihydrate (0.32 g), phenol (0.15 g), anhydrous potassium carbonate (0.22 g) and potassium iodide (catalytic trace) in 4-methyl-2-pentanone (125 ml) were stirred under reflux for 18 hours. Further portions of phenol, anhydrous potassium carbonate and potassium iodide were then added thrice at 8 hour intervals, followed by a final 18 hours refluxing. After cooling, methylene chloride (50 ml) and methanol (20 ml) were added and the reaction mixture filtered. The filtrate was evaporated in vacuo and the residue dissolved in methylene chloride, washed with water, dried (MgSO$_4$) and evaporated in vacuo. Chromatography on silica (Merck 9385, 40 g) eluting with methylene chloride/methanol (100:0→88:12) followed by treatment of the product with ethereal hydrogen chloride and recrystallisation from isopropanol gave 4-amino-6,7-dimethoxy-2-[4-(2-phenoxypyrimidin-4-yl)piperazin-1-yl]quinoline dihydrochloride (0.26 g), m.p. 199°–201° (d).

Analysis %: Found: C, 56.1; H, 5.2; N, 15.7. Calculated for C$_{25}$H$_{26}$N$_6$O$_3$.2HCl: C, 56.5; H, 5.3; N, 15.8.

EXAMPLE 28

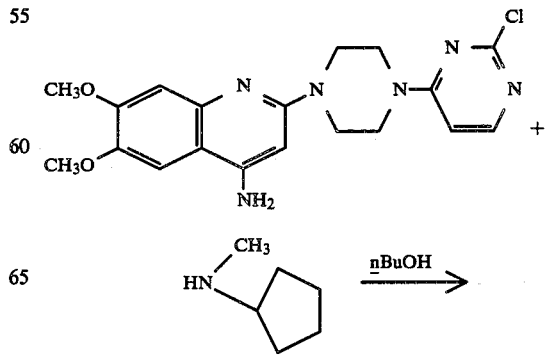

-continued

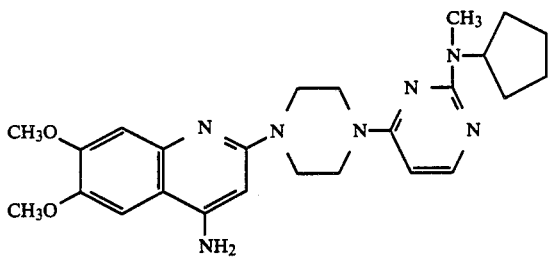

4-Amino-2-[4-(2-chloropyrimidin-4-yl)piperazin-1-yl]-6,7-dimethoxyquinoline hemihydrate (0.2 g) and N-methylcyclopentylamine (0.17 g) in n-butanol (20 ml) were stirred under reflux for 60 hours. The mixture was then evaporated in vacuo, the residue partitioned between chloroform and sodium carbonate solution (10%) and the aqueous phase extracted with chloroform. The combined extracts were washed with water, dried (MgSO₄), evaporated in vacuo and the residue chromatographed on silica gel (Merck 9385, 50 g). Elution with methylene chloride/methanol (100.0→85:15) followed by treatment of the product with ethereal hydrogen chloride and recrystallisation from isopropanol/ether gave 4-amino-6,7-dimethoxy-2-[4-(2-N-methylcyclopentylaminopyrimidin-4-yl)piperazin-1-yl]quinoline dihydrochloride sesquihydrate (0.06 g), m.p. 248°–250°.

Analysis %: Found: C, 53.6; H, 6.5; N, 17.2. Calculated for $C_{25}H_{33}N_7O_2.2HCl.1.5H_2O$: C, 53.3; H, 6.8; N, 17.4.

EXAMPLE 29

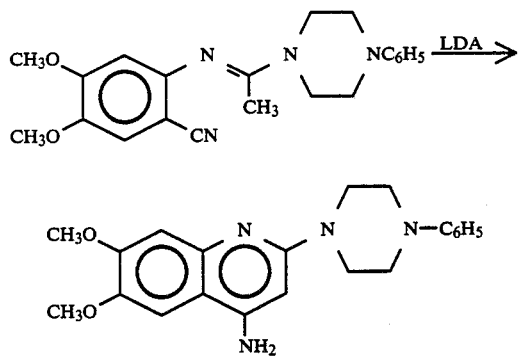

N-[1-(4-Phenylpiperazin-1-yl)ethylidene]-2-cyano-4,5-dimethoxyaniline (2.5 g) in tetrahydrofuran (35 ml) was added to a stirred solution of lithium diisopropylamide [from n-butyl lithium 1.3M in hexane (6.44 ml) and diisopropylamine (1.44 ml)] in tetrahydrofuran (5 ml) at −70°. The resulting solution was stirred at −70° for 4 hours then allowed to attain room temperature overnight. The mixture was poured into ice-water (100 ml), extracted with chloform (3×200 ml), the combined extracts washed with water, dried (Na₂SO₄) and evaporated in vacuo. The residue was taken up in chloroform/methanol, treated with ethereal hydrogen chloride and recrystallised from methanol to give 4-amino-6,7-dimethoxy-2-[4-phenylpiperazin-1-yl]quinoline dihydrochloride hemihydrate (0.82 g) m.p. 288°–290°.

Analysis %: Found: C, 56.9; H, 6.0; N, 12.7. Calculated for $C_{21}H_{24}N_4O_2.2HCl.\frac{1}{2}H_2O$: C, 56.5; H, 6.1; N, 12.6.

EXAMPLES 30 TO 32

The following compounds were prepared by the same general route as in Example 27, using the appropriate substituted ethylidene compound of formula (II), except that in Example 31 the reaction was completed by heating on a steam bath. In Examples 30 and 32, the crude product was purified by column chromatography.

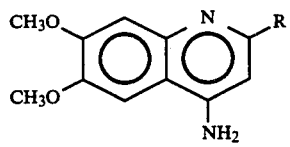

| Example No. | R | Form isolated m.p. | Analysis % (Theoretical in brackets) | | |
|---|---|---|---|---|---|
| | | | C | H | N |
| 30 | —N⟨piperidine⟩ | HCl, 272–275° | 58.9 (59.3 | 6.9 6.9 | 13.1 13.0) |
| 31 | —N(CH₃)(CH₃) | HCl.½H₂O 285–288° | 53.8 (53.3 | 6.3 6.5 | 14.6 14.4) |
| 32 | —N⟨piperazine⟩NH | 2HCl.½H₂O 260° | 47.8 (47.5 | 6.0 6.4 | 15.1 14.8) |

EXAMPLE 33

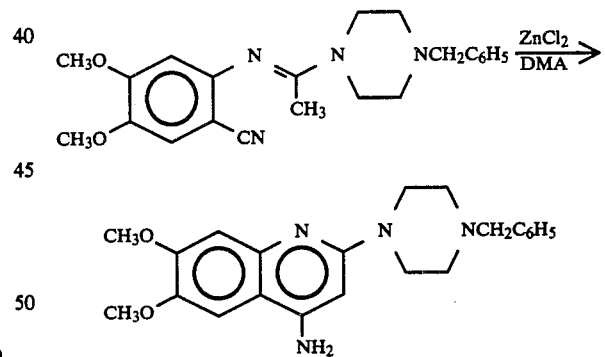

N-[1-(4-Benzylpiperazin-1-yl)ethylidene]-2-cyano-4,5-dimethoxyaniline (13.5 g) and zinc chloride (4.86 g) in dimethylacetamide (90 ml) were stirred under reflux for 2½ hours; further zinc chloride (0.5, 0.2 g) was added after ½ and 1½ hours respectively. The mixture was cooled, treated with ether (700 ml, 2×100 ml) and the supernatant discarded each time. The residual tar was then treated with sodium hydroxide solution (2N, 100 ml) and methylene chloride (100 ml) and the mixture was stirred at room temperature for 5 minutes. The organic layer was separated, the aqueous phase extracted with methylene chloride and the total organic extracts washed with water. The dried (Na₂SO₄) extracts were evaporated in vacuo and the brown residue (∼13 g) purified by chromatography on silica gel (Merck 9385, 250 g) eluting with chloroform-methanol (100:0→88:12). A sample of the pure product (6.95 g) was taken up in ethanol, treated with ethereal hydrogen chloride and evaporated in vacuo. The residue was recrystallised from methanol to give 4-amino-6,7-dimethoxy-2-(4-benzylpiperazin-1-yl)quinoline dihydrochloride sesquihydrate, m.p. 260°-263°.

Analysis %: Found: C, 54.9; H, 5.9; N, 11.5. Calculated for $C_{22}H_{26}N_4O_2.2HCl.1\frac{1}{2}H_2O$: C, 55.2; H, 6.5; N, 11.7.

EXAMPLE 34

4-Amino-6,7-dimethoxy-2-[6,7-dimethoxy-1,2,3,4-tetrahydroisoquinol-2-yl]quinoline, m.p. 226°-227° was prepared in the same general manner as the previous Example using the corresponding 1-[6,7-dimethoxy-1,2,3,4-tetrahydroisoquinol-2-yl]ethylidene compound except that the crude reaction residue was recrystallised from isopropanol.

Analysis %: Found: C, 66.0; H, 6.3; N, 10.9. Calculated for $C_{22}H_{25}N_3O_4$: C, 66.8; H, 6.4; N, 10.6.

EXAMPLE 35

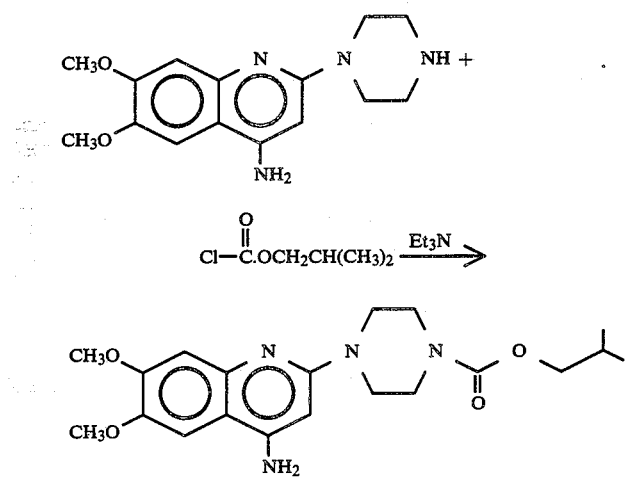

A solution of isobutylchloroformate (0.11 g) in chloroform (5 ml) was added dropwise to a stirred solution of 4-amino-6,7-dimethoxy-2-[piperazin-1-yl]quinoline (0.21 g) in chloroform (15 ml) with triethylamine (0.22 g) at 10°. The solution was then stirred at room temperature for 1 hour and sodium carbonate solution (10%, 10 ml) added. The organic phase was separated, the aqueous solution extracted with chloroform (2×15 ml) and the total combined extracts dried ($Na_2SO_4$) and evaporated in vacuo. The residue was purified by chromatography on silica gel (Merck 9385, 25 g) eluting with methylene chloride-methanol (100:0→93:7), followed by treatment of the product with ethereal hydrogenchloride and recrystallisation from isopropanol to give 4-amino-6,7-dimethoxy-2-[4-(isobutoxycarbonyl)-piperazin-1-yl]quinoline hydrochloride sesquihydrate, m.p. 254°-256° (0.065 g).

Analysis %: Found: C, 52.8; H, 6.9; N, 12.2. Calculated for $C_{20}H_{28}N_4O_4.HCl.1\frac{1}{2}H_2O$: C, 53.2; H, 7.1; N, 12.4.

EXAMPLES 36 TO 39

The following compounds were prepared similarly to Example 35, using the appropriate chloroformate $ClCOOR_3$ as indicated, the product being crystallised from the solvent shown in each case. The compound of Example 38 was obtained as a bi-product from Example 37, ethyl chloroformate having been formed in situ due to traces of ethanol in the chloroform reaction solvent.

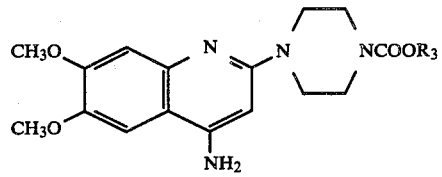

| Example No. | $R^3$ | Form Isolated and m.p. (°C.) | Prepared from and recrystallised from | Analysis % (Theoretical in brackets) | | |
|---|---|---|---|---|---|---|
| | | | | C | H | N |
| 36 | $-CH_2C(CH_3)=CH_2$ | HCl $H_2O$, 244-245° C. dec. | 2-methylallyl chloroformate (1), IPA | 54.8 (54.5 | 6.2 6.6 | 12.7 12.7) |
| 37 | $-CH_2CH_3$ | HCl 0.5 $H_2O$, 278-279° C. | Ethyl chloroformate (2), IPA | 53.5 (53.3 | 6.3 6.5 | 13.8 13.8) |
| 38 | -C₆H₄-F (p-F-phenyl) | HCl, 285° C. | p-Fluorophenyl chloroformate, MeOH | 56.9 (57.1 | 5.2 5.2 | 12.1 12.1) |
| 39 | $-CH_2$-C₆H₅ | HCl 1.5 $H_2O$, 204-206° C. dec. | Benzyl chloroformate, MeOH | 57.2 (56.8 | 5.8 6.2 | 12.0 11.5) |

(1) Prepared in situ.
(2) Formed in situ.

EXAMPLE 40

2-Methylallyl 4-[4-amino-6,7-dimethoxyquinolin-2-yl]piperazine-1-carboxylate (0.21 g) was added to a stirred solution of concentrated sulphuric acid (2 ml) and $H_2O$ (2 ml) at 10°-15° and stirring maintained at 10°-15° for 3 hours. The reaction mixture was basified with sodium hydroxide solution (5N) whilst maintaining temperature below 15° and then extracted with methylene chloride. The combined extracts were washed with water, dried ($MgSO_4$) and evaporated in vacuo. Chromatography on silica (Merck 9385, 100 g) eluting with methylene chloride/methanol (100:0→85:15) followed by treatment of the product with ethereal hydrogen chloride and recrystallisation from isopropanol gave 2-methyl-2-hydroxypropyl 4-[4-amino-6,7-dimethoxyquinolin-2-yl]piperazine-1-carboxylate hydrochloride hemihydrate (0.05 g), m.p. 280°.

Analysis %: Found: C, 53.6; H, 6.6; N, 12.7. Calculated for $C_{20}H_{28}N_4O_5.HCl.0.5H_2O$: C, 53.4; H, 6.7; N, 12.5.

EXAMPLE 41

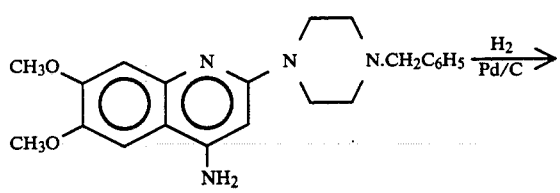

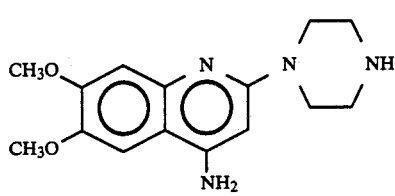

4-Amino-6,7-dimethoxy-2-(4-benzylpiperazin-1-yl)quinoline (6.2 g) in ethanol (300 ml) with 5% Pd/C catalyst was stirred at 50° under an atmosphere of hydrogen (50 p.s.i.) for 20 hours. The mixture was cooled, chloroform (100 ml) added and the solution filtered through "Solkafloc". The solid was washed with chloroform-methanol (1:1, 4×100 ml) and the combined filtrates evaporated in vacuo. The residue was partitioned between chloroform-sodium carbonate solution (10%), the organic layer removed, the aqueous phase saturated with salt and further extracted with chloroform. The combined organic extracts were washed with brine, dried ($Na_2SO_4$) and evaporated in vacuo to yield 4-amino-6,7-dimethoxy-2-(piperazin-1-yl)quinoline (2.42 g). Spectroscopy showed this product to be the same as that of Example 32.

The following Preparations illustrate the preparation of certain starting materials.

PREPARATION 1

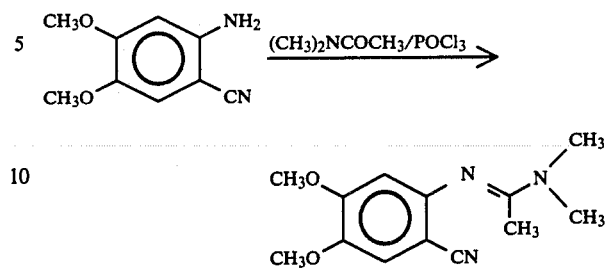

Phosphorous oxychloride (1.0 ml) was added to a stirred solution of dimethylacetamide (2.8 ml) in chloroform (10 ml) at room temperature. The mixture was stirred for 5 minutes, 2-cyano-4,5-dimethoxyaniline (1.78 g) added and the reaction stirred under reflux for 4 hours. The mixture was cooled, poured onto ice and extracted with chloroform and the organic phase discarded. The aqueous layer was basified (solid NaOH) extracted with chloroform, the combined extracts washed with water, dried ($Na_2SO_4$) and evaporated in vacuo. A sample of the brown oily residue (2 g) was crystallised from diisopropylether to give N,N-dimethyl-N'-(2-cyano-4,5-dimethoxyphenyl)acetamidine, m.p. 94°–96°.

Analysis %: Found: C, 63.3; H, 6.9; N, 17.2. Calculated for $C_{13}H_{17}N_3O_2$: C, 63.1; H, 6.9; N, 17.0.

The following compounds were prepared by the same general method as Preparation 1, starting from the appropriate acetyl derivative of the formula $R.COCH_3$. In Preparation 2 the crude product was purified by column chromatography.

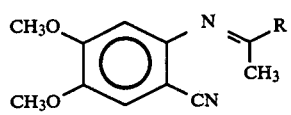

| Preparation No. | R | Form Isolated m.p. | Molecular Formula | Analysis % (Theoretical in brackets) | | |
|---|---|---|---|---|---|---|
| | | | | C | H | N |
| 2 | —N⟨piperidine⟩ | crude | Characterised by spectroscopy | | | |
| 3 | —N⟨N—C₆H₅⟩ piperazine | free base 108–109° | $C_{21}H_{24}N_4O_2$ | 69.2 (69.2 | 6.7 6.6 | 15.3 15.4) |
| 4 | —N⟨NCOCF₃⟩ | free base 136–138° | $C_{17}H_{19}N_4O_3F_3$ | 52.9 (53.1 | 4.9 5.0 | 14.7 14.6) |
| 5 | —N⟨tetrahydroisoquinoline-OCH₃,OCH₃⟩ | free base 143–145° | $C_{22}H_{25}N_3O_4$ | 66.0 (66.8 | 6.3 6.4 | 10.5 10.6) |

PREPARATION 6

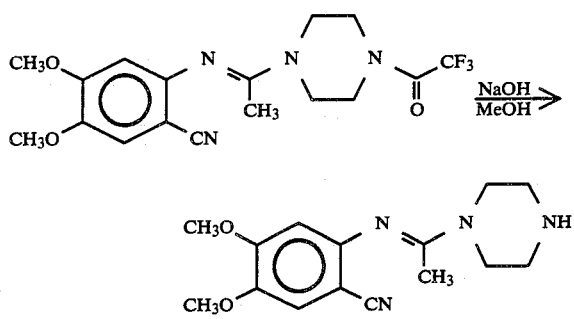

A solution of N-[1-(4-trifluoroacetylpiperazin-1-yl)ethylidene]-2-cyano-4,5-dimethoxyaniline (29.5 g) in methanol (400 ml) and sodium hydroxide (2N, 100 ml) was stirred at room temperature for 3 hours. The mixture was then evaporated in vacuo, the residue taken up in chloroform (350 ml) washed with water and dried ($Na_2SO_4$). The solution was evaporated in vacuo and the crude N-(1-[piperazin-1-yl]ethylidene)-2-cyano-4,5-dimethoxyaniline (23 g), used without further purification.

PREPARATION 7

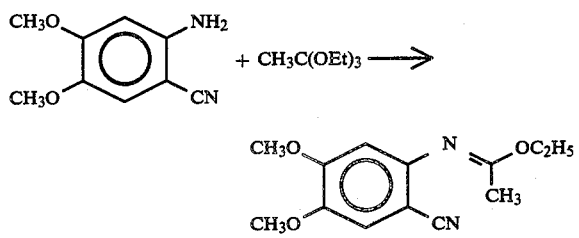

2-Cyano-4,5-dimethoxyaniline (20 g), a trace of the corresponding hydrogen chloride salt (200 mg) and triethylorthoacetate (40 ml) were stirred at 150° for 1 hour, with removal of ethanol by distillation. The mixture was then evaporated in vacuo and the crude residue of ethyl N-(2-cyano-4,5-dimethoxyphenyl)acetimidate (27.95 g) used directly.

PREPARATION 8

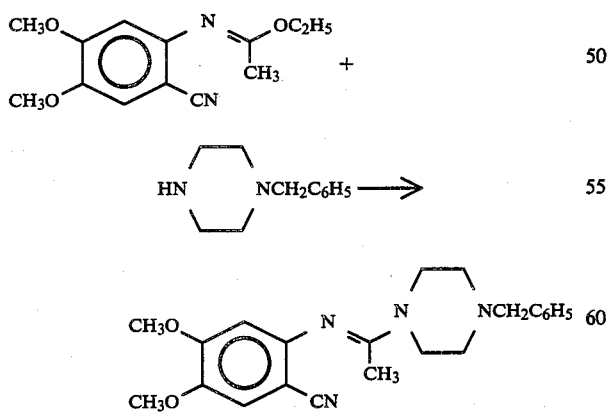

The crude product (26.9 g) from the previous Preparation, N-benzylpiperazine (21 g) and p-toluenesulphonic acid (100 mg) were stirred together at 150° for 2 hours under a slight pressure reduction. On cooling, the residue was taken up in methylene chloride and extracted with dilute hydrochloric acid (2N, 2×200 ml). The acid layer was adjusted to pH4 (5N NaOH), extracted with methylene chloride (2×200 ml) and the combined extracts discarded. The aqueous phase was then basified to pH9, extracted with methylene chloride (3×200 ml), the combined extracts washed with brine, dried ($Na_2SO_4$) and evaporated in vacuo. The residue was purified by column chromatography (Merck 9385 silica, 400 g) eluting with methylene chloride/methanol (100:0→98:2) and a sample of the product (11.68 g) was taken up in ethyl acetate-methanol and treated with ethereal hydrogen chloride. The solid was treated with ether and dried to give N-[1-(4-benzylpiperazin-1-yl)ethylidene]-2-cyano-4,5-dimethoxyaniline dihydrochloride hydrate, m.p. 181°-182°.

Analysis %: Found: C, 56.6; H, 6.7; N, 11.9. Calculated for $C_{22}H_{26}N_4O_2 2HCl.H_2O$: C, 56.3; H, 6.4; N, 11.9.

We claim:

1. A compound of the formula:

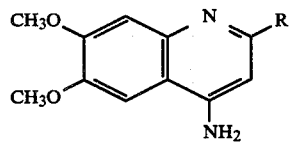

and the pharmaceutically acceptable acid addition salts thereof, where R is a group of the formula:

wherein Y is —$COR^1$ and $R^1$ is $C_1$–$C_6$ alkyl, aralkyl having up to ten carbon atoms in the nuclear ring with up to four carbon atoms in the alkyl moiety, $C_3$–$C_6$ cycloalkyl, ($C_3$–$C_6$ cycloalkyl)methyl, aryl having up to ten carbon atoms in the nuclear ring, styryl, quinolyl, furyl, tetrahydrofuryl, 1,4-benzodioxan-2-yl, chroman-2-yl or 5-methylthio-1,3,4-oxadiazol-2-yl, and each aryl group is naphthyl, phenyl or ring-substituted phenyl having up to two substituents each selected from halo, $CF_3$, $C_1$–$C_4$ alkyl or $C_1$–$C_4$ alkoxy or one substituent which is methylenedioxy.

2. A compound as claimed in claim 1 wherein $R^1$ of —$COR^1$ is methyl, cyclopentyl, cyclopropylmethyl, 2-naphthyl, phenyl, p-fluorophenyl, 3,4-methylenedioxyphenyl, styryl, 2-quinolyl, 2-furyl, 1,4-benzodioxan-2-yl or chroman-2-yl.

3. A compound as claimed in claim 1 wherein R is 4-(2-furoyl)piperazin-1-yl or 4-(1,4-benzodioxan-2-carbonyl)piperazin-1-yl.

4. 4-Amino-2-[4-(2-furoyl)piperazin-1-yl]-6,7-dimethoxyquinoline.

5. 4-Amino-2-[4-(1,4-benzodioxan-2-carbonyl)piperazin-1-yl]-6,7-dimethoxyquinoline.

6. A pharmaceutical composition suitable for oral or parenteral administration comprising a pharmaceutically acceptable carrier and an effective antihypertensive amount of a compound as claimed in claim 1.

7. A method for lowering blood pressure in the treatment of a hypertensive subject, which comprises administering to said subject an effective blood pressure lowering amount of a compound as claimed in claim 1.

* * * * *